(12) United States Patent
Ouchi

(10) Patent No.: US 6,261,284 B1
(45) Date of Patent: Jul. 17, 2001

(54) CONNECTING STRUCTURE FOR ENDOSCOPIC TREATMENT TOOL

(75) Inventor: Teruo Ouchi, Saitama (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/286,677

(22) Filed: Apr. 6, 1999

(30) Foreign Application Priority Data

Apr. 10, 1998 (JP) .................................................. 10-098868

(51) Int. Cl.[7] ...................................................... A61B 1/00
(52) U.S. Cl. ............................... 606/1; 600/121; 600/125
(58) Field of Search ................................. 606/1; 600/121, 600/125, 159, 139, 136, 144

(56) References Cited

U.S. PATENT DOCUMENTS 5,140,975 * 8/1992 Krauter ....................................... 128/4
5,499,985 * 3/1996 Hein et al. ............................... 606/99
5,707,342 * 1/1998 Tanaka .................................... 600/114
6,113,586 * 9/2000 Ouchi ....................................... 606/1

FOREIGN PATENT DOCUMENTS

| 54-10796 | 5/1979 | (JP) . |
| 62-14810 | 4/1987 | (JP) . |
| 1-33048 | 10/1989 | (JP) . |
| 2-1499 | 1/1990 | (JP) . |

* cited by examiner

Primary Examiner—Linda C. M. Dvorak
Assistant Examiner—Jocelyn Debra Ram
(74) Attorney, Agent, or Firm—Greenblum & Bernstein, P.L.C.

(57) ABSTRACT

A flexible sheath that is to be inserted into or removed from a treatment tool insertion channel of an endoscope has a thick portion formed locally near the base end. The thick portion has a larger outside diameter than the other portions. The base end of the flexible sheath 1 is inserted into a connection member which is to be connected to the base end. The thick portion and an adjacent portion of the connection member are pressure-inserted in series into a soft coupling tube to fix the connection between the flexible sheath and the connection member.

15 Claims, 6 Drawing Sheets

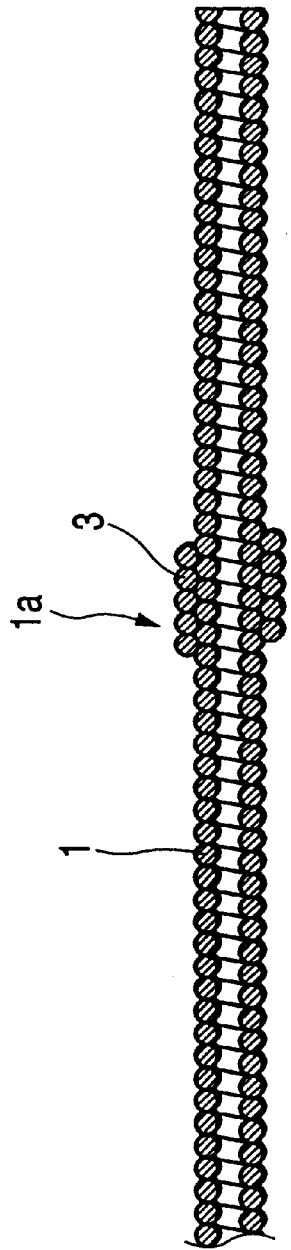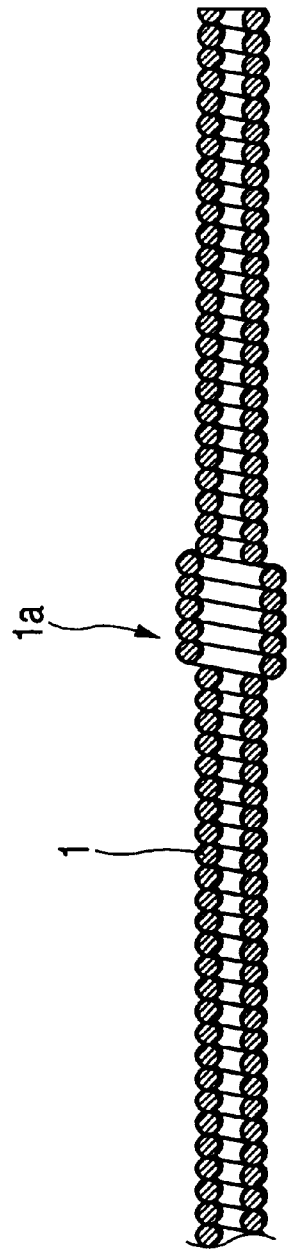

CONNECTING STRUCTURE FOR ENDOSCOPIC TREATMENT TOOL

BACKGROUND OF THE INVENTION

The present invention relates to a connecting structure for an endoscopic treatment tool, and in particular to a connecting structure capable of fixing the connection between a flexible sheath and a connection member to be connected to the base end of the flexible sheath.

Common forms of the flexible sheath of an endoscopic treatment tool are tightly wound coil pipes that are formed by winding many turns of stainless steel wire on close pitches to have a specified diameter. The base end of the coil pipe is connected and fixed to the hand-operated manipulating section of the endoscopic treatment tool by soldering, spot welding, silver brazing or any other suitable securing means.

However, connecting and fixing the base end of the flexible sheath to the hand-operated manipulating section by soldering, spot welding or silver brazing involves cumbersome operations. In addition, if a manipulating wire is already passed through the flexible sheath, troubles may occur in which the wire is undesirably fixed, twisted or damaged. Further, the disassembly and repair work is not easy to perform.

SUMMARY OF THE INVENTION

An object, therefore, of the invention is to provide a connecting structure for an endoscopic treatment tool, with which the connection between a flexible sheath and a connection member can be fixed in an easy, positive manner without using common solder, silver solder or any other securing materials.

The stated object of the invention can be attained by the following arrangement. A thick portion is provided on the flexible sheath. The thick portion of the flexible sheath and a portion of the connection member are disposed in series and pressure-inserted into a soft coupling tube. This arrangement makes it possible to fix the connection between the flexible sheath and the connection member in an easy, positive manner without using common solder, silver solder or any other securing materials.

In a preferable embodiment, a connecting structure for an endoscopic treatment tool has a flexible sheath to be inserted into or removed from a treatment tool insertion channel of an endoscope. The flexible sheath has a thick portion that is formed locally adjacent its base end and that has a larger outside diameter than the other portions. The base end of said flexible sheath is inserted into a connection member which is to be connected to the base end. The thick portion and an adjacent portion of said connection member to the thick portion are disposed in series and pressure-inserted into a soft coupling tube, to thereby fix the connection between said flexible sheath and said connection member.

The thick portion may be formed by securing a tubular member around the flexible sheath. Alternatively, the thick portion may be formed by increasing the outside diameter of the flexible sheath locally.

The thick portion may be in contact with an end face of the connection member. Alternatively, the thick portion may partly be inserted into the connection member.

The outer surface of that portion of the connection member which is to be pressure-inserted into the coupling tube is formed in such a shape that said portion engages the inner circumference of the coupling tube in a direction opposite to the direction of the pressure-insertion. The flexible sheath may be a tightly wound coil pipe or a flexible tube.

The present disclosure relates to the subject matter contained in Japanese patent application No. Hei. 10-98868 (filed on Apr. 10, 1998), which is expressly incorporated herein by reference in its entirety.

BRIEF DESCRIPTION OF THE DRAWINGS

In the accompanying drawings:

FIG. 3 shows a longitudinal section of a modification of the thick portion of the flexible sheath according to the first embodiment;

FIG. 4 shows a longitudinal section of another modification of the flexible sheath according to the first embodiment;

DETAILED DESCRIPTION OF THE CONNECTING STRUCTURE

Figure 1:
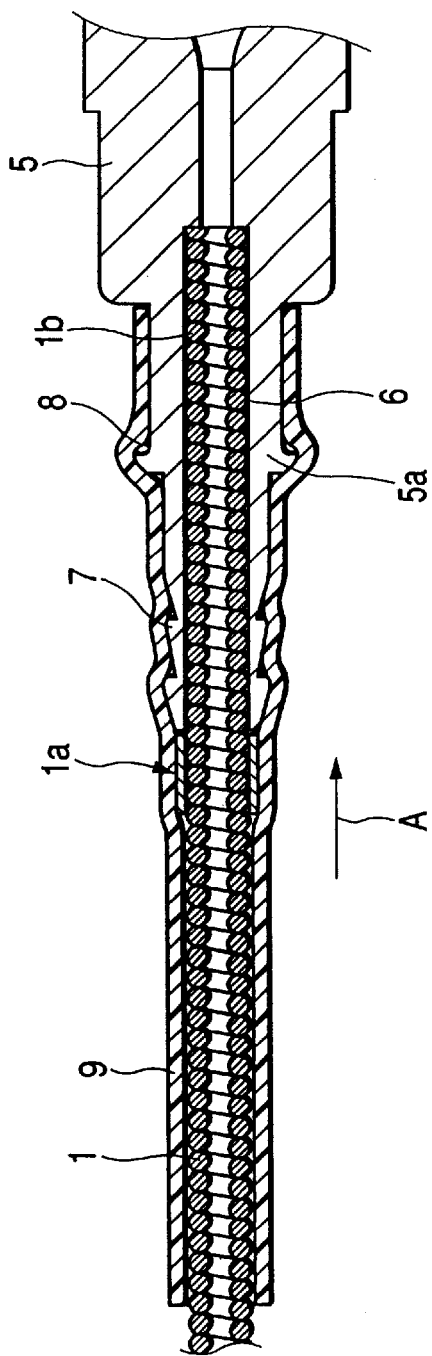
FIG. 1 shows a longitudinal section of a connecting structure for an endoscopic treatment tool according to the first embodiment.

FIG. 1 shows a connecting structure for an endoscopic treatment tool according to a first embodiment. Indicated by 1 is a flexible sheath of the endoscopic treatment tool, which is to be inserted into or removed from a treatment tool insertion channel (not shown) of an endoscope. The sheath 1 is made up of a coil pipe that is formed by tightly winding many turns of stainless steel wire on close pitches to have a specified diameter.

Figure 2:
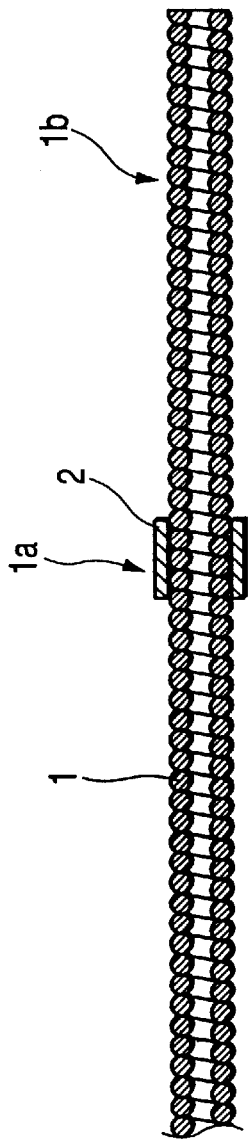
FIG. 2 shows a longitudinal section of the thick portion of the flexible sheath according to the first embodiment.

As shown in FIG. 2, a thick portion or radially expanded portion 1a is locally provided around the flexible sheath 1 and located adjacent to a base end 1b of the flexible sheath 1. The thick portion 1a be formed by preliminarily bonding, soldering or otherwise securing a tubular member 2 in the form of a metal pipe onto the flexible sheath 1. The thick portion 1a has a larger outside diameter than any other part of the flexible sheath 1.

The thick portion 1a may be formed by securing a thick and short tightly wound coil 3 or the like around the flexible sheath 1 as shown in FIG. 3. Alternatively, the thick portion 1a may be formed by locally increasing the diameter of each turn of the flexible sheath 1 as shown in FIG. 4.

Turning back to FIG. 1, reference numeral 5 indicates a connection member of an endoscopic treatment tool, which is to be connected to the base end 1b of the flexible sheath 1. The connection member 5 is typically a connecting socket for connecting the flexible sheath 1 to the hand-operated manipulating section. The connection member 5 may be the hand-operated manipulating section per se. A sheath receiving hole 6 is formed in an end portion 5a of the connection member 5, and thus the end portion 5a of the connection member 5 is hollow tubular. The base end 1b of the flexible sheath 1 is fitted into the hole 6.

The end portion 5a of the connection member 5 is concentric to the longitudinal axis of the sheath receiving hole 6, and has a radially expanded portion (in the form of a sawtoothed edge 7) and a step 8 formed in series on the outer circumference thereof in order to provide the positive engagement of the end portion 5a with a coupling tube 9 to be described below.

The base end 1b of the flexible sheath 1 is fitted into the sheath receiving hole 6 so that the thick portion 1a comes in contact with an end face of the connection member 5. Then, the part between the connection member 5 and the flexible sheath 1 is covered with a coupling tube 9 as shown in FIG. 1.

The coupling tube 9 is a flexible tube that is typically made of a tetrafluoroethylene resin, a polyethylene resin or nylon. Its inside diameter is slightly larger that the outside diameter of the flexible sheath 1 but smaller than the outside diameter of the thick portion 1a.

Because of these dimensional relationships, if the flexible sheath 1 is passed through the coupling tube 9 (that is, the coupling tube 9 is moved in the direction of arrow A with respect to the flexible sheath 1) until the inner surface of the coupling tube 9 contacts the thick portion 1a, the coupling tube 9 is spread or expanded by the thick portion 1a. Thus, the thick portion 1a has been pressure-inserted into the coupling tube 9.

Then, the coupling tube 9 is further moved in the direction of arrow A, and the sawtoothed edge 7 and step 8 of the connection member 5 are pressure-inserted into the coupling tube 9 and held in series with respect to the thick portion 1a of the flexible sheath 1, whereupon the coupling tube 9 is fixed to the connection member 5 with thick portion 1a being urged against an end face of the connection member 5 (see FIG. 1).

Once this condition is attained, the connection between the coupling tube 9 and the connection member 5 is stable since the sawtoothed edge 7 and the step 8 each come in engagement with or bite into the inner circumference of the coupling tube 9 when an external force is applied in a direction opposite to the direction in which the thick portion 1a of the flexible sheath 1 has been pressed into the coupling tube 9.

The coupling tube 9 is typically formed in a length of about 5 to 10 cm and it also functions as a so-called "anti-bent means" which prevents the flexible sheath 1 from bending abruptly near the connection to the connection member 5, thereby ensuring that it will not acquire the tendency to bend.

The coupling tube 9 is such that the thick portion 1a of the flexible sheath 1 and the sawtoothed edge 7 and the step 8 of the connection member 5 have been pressed in series into the end portion of the coupling tube 9 but nothing has been pressed into the other parts of the coupling tube 9, which therefore can bend in every direction. This ensures that irrespective of the direction in which the coupling tube 9 is bent, there occurs no change in the firmness of the connection between the base end 1b of the flexible sheath 1 and the connection member 5.

Thus, the connection between the base end 1b of the flexible sheath 1 and the connection member 5 can be fixed simply and positively by the pressure-insertion into the coupling tube 9. If it is necessary to disassemble the connected parts, one may cut open the coupling tube 9 with a razor blade or the like. The parts can be reassembled by fixing the flexible sheath 1 using another coupling tube 9.

Figure 5:
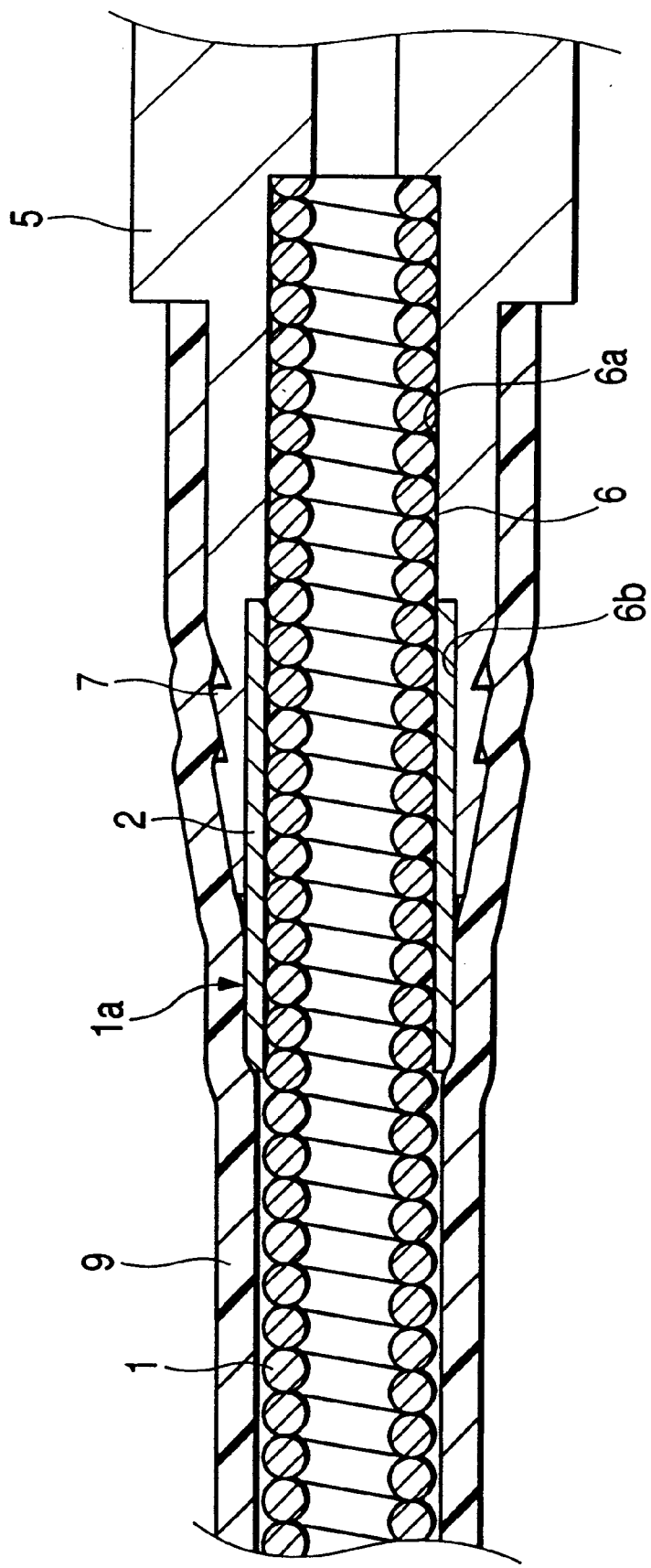
FIG. 5 shows a longitudinal section of a connecting structure for an endoscopic treatment tool according to the second embodiment.

FIG. 5 shows a connecting structure for an endoscopic treatment tool according to a second embodiment. The sheath receiving hole 6 of the connection member 5 is constructed by a small inside diameter portion 6a and a large inside diameter portion 6b that is larger in inside diameter than the small inside diameter portion and contiguous to an opening end of the connection member 5. The tubular member 2 forming the thick portion 1a is partially inserted and fitted into the large-diameter portion 6b. This contributes to reinforce the boundary portion of the connection between the flexible sheath 1 and the connection member 5.

Figure 6:
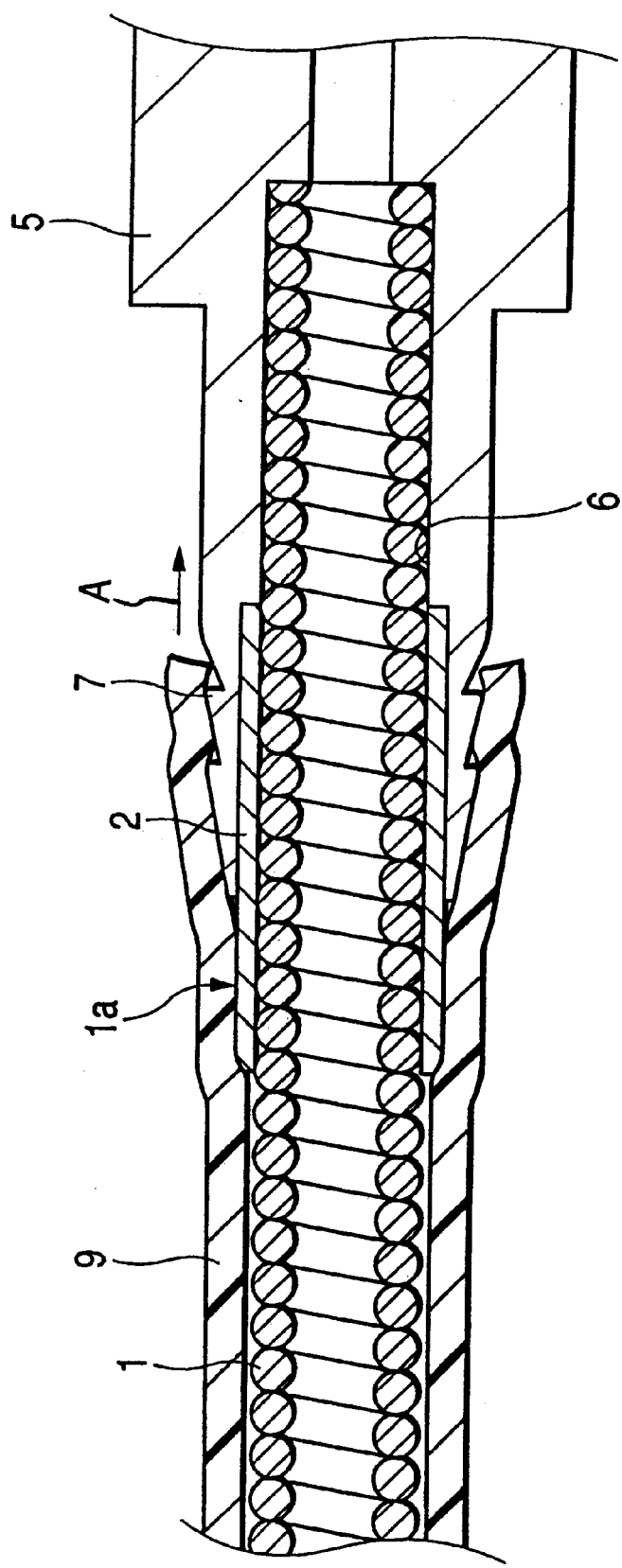
FIG. 6 shows, in longitudinal section, an intermediate step in the process of assembling the connecting structure according to the second embodiment.

The other parts of the second embodiment have the same configuration as in the first embodiment except that the connection member 5 does not have the step 8. FIG. 6 shows an intermediate step in the process of pressure-inserting the thick portion 1a of the flexible sheath 1 and the sawtoothed edge 7 of the connection member 5 into the coupling tube 9 in the second embodiment.

Figure 7:
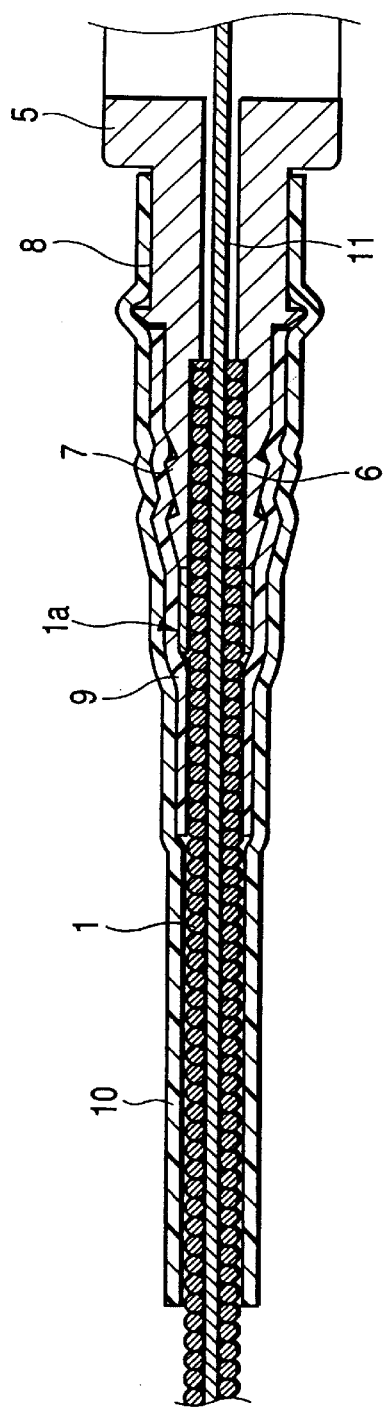
FIG. 7 shows a longitudinal section of a connecting structure for an endoscopic treatment tool according to the third embodiment.

FIG. 7 shows a connecting structure for an endoscopic treatment tool according to a third embodiment, in which an anti-bend tube 10 is provided as a separate member from the coupling tube 9 made of a soft material.

The thick portion 1a of the flexible sheath 1 and the sawtoothed edge 7 of the connection member 5 are pressure-inserted into the coupling tube 9, and the anti-bent tube 10 is covered over the coupling tube 9 such that the step 8 of the connection member 5 is pressure-inserted into the base end of the anti-bend tube 10. Indicated by 11 is a manipulating wire that is moved back and forth along the longitudinal axis in the hand-operated manipulating section 5.

Figure 8:
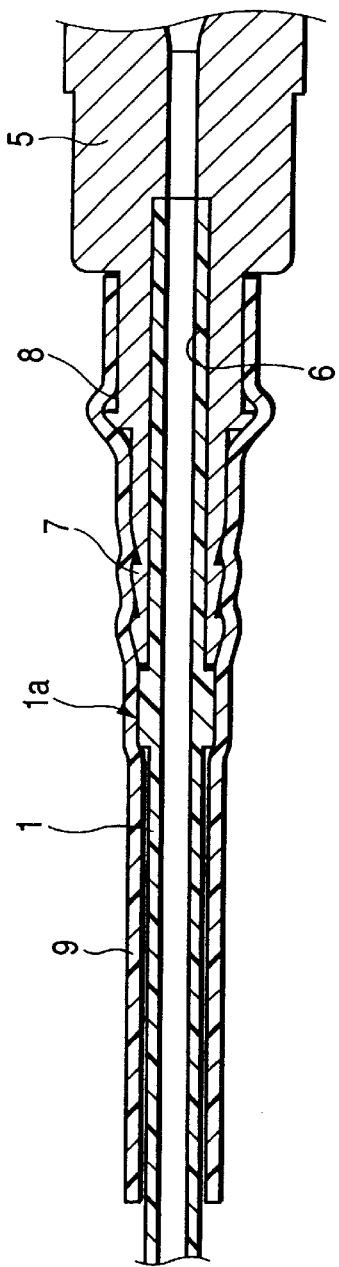
FIG. 8 shows a longitudinal section of a connecting structure for an endoscopic treatment tool according to the fourth embodiment.

FIG. 8 shows a connecting structure for an endoscopic treatment tool according to a fourth embodiment, in which the flexible sheath 1 formed of a tube rather than a tightly wound coil pipe has its wall thickness increased outwardly in a certain area than in the other areas to thereby form the thick portion 1a. In the case under consideration, the connection member 5 is typically used as a syringe needle receptacle, and the other parts of the fourth embodiment have the same configuration as in the first embodiment.

Figure 9:
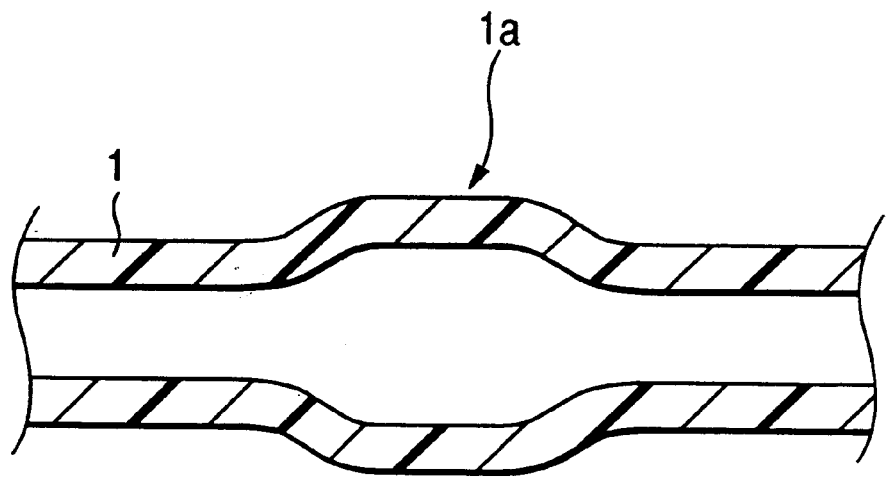
FIG. 9 shows a longitudinal section of a modification of the thick portion of the flexible sheath according to the fourth embodiment.
Figure 10:
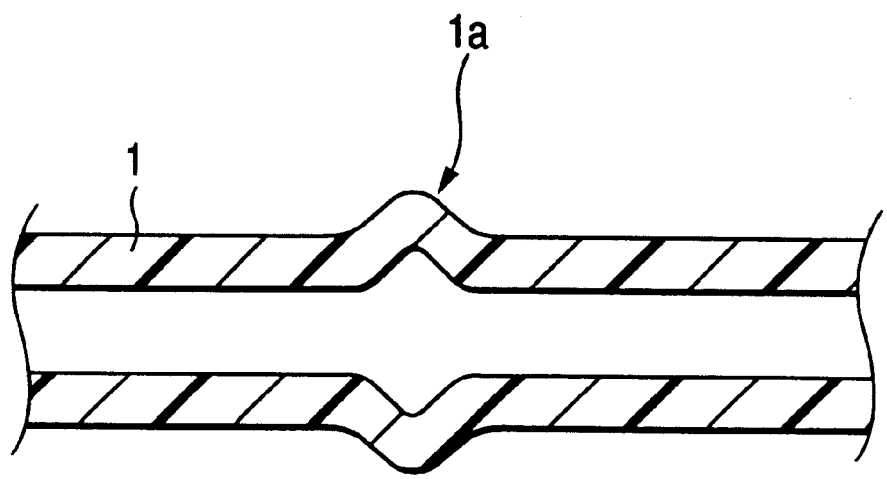
FIG. 10 shows a longitudinal section of another modification of the thick portion of the flexible sheath according to the fourth embodiment.

If the flexible sheath 1 is to be formed of a tube, its wall thickness need not be varied as described above; instead, the flexible sheath 1 may be bulged outward locally to form the thick portion 1a as shown in FIGS. 9 and 10.

What is claimed is:

1. A connecting structure for an endoscopic treatment tool, comprising:
    a flexible sheath having a base end and a first radially expanded portion adjacent to said base end;
    a connection member having a hollow tubular end portion, said hollow tubular portion having a hole receiving said base end, and a second radially expanded portion on its outer circumference; and
    a tube covering and holding at least said first and second radially expanded portions under pressure.

2. A connecting structure for an endoscopic treatment tool having a connection member and a flexible coupling tube, the connecting structure comprising a flexible sheath, said flexible sheath configured for insertion into or removal from an endoscopic treatment tool insertion channel of an endoscope, said flexible sheath comprising:

a base end disposed within the connection member; and a thickened portion adjacent to said base end and a portion of the connection member within which said base end is disposed, said thickened portion having an outer diameter larger than other portions of said flexible sheath;

wherein said thickened portion and said portion of the connection member within which said base end is disposed are arranged in series and are configured to be inserted into the flexible coupling tube.

3. The connecting structure according to claim 2, wherein said thickened portion comprises a tubular member disposed about said flexible sheath.

4. The connecting structure according to claim 2, wherein said thickened portion is formed by increasing an outer diameter of said flexible sheath.

5. The connecting structure according to claim 2, wherein said thickened portion contacts an end face of the connection member.

6. The connecting structure according to claim 5, wherein:

said thickened portion and said portion of the connection member configured to be inserted into the flexible coupling tube are configured to be inserted into the flexible coupling tube in a predetermined direction; and an outer surface of said portion of the connection member configured to be inserted into the flexible coupling tube is configured to engage an inner circumference of said coupling tube in a direction opposite to said predetermined direction.

7. The connecting structure according to claim 6, wherein said flexible sheath one of a tube or a wound coil pipe.

8. The connecting structure according to claim 5, wherein said flexible sheath is one of a tube or a wound coil pipe.

9. The connecting structure according to claim 2, wherein a portion of said thickened portion is disposed within the connection member.

10. The connecting structure according to claim 9, wherein:

said thickened portion and said portion of the connection member configured to be inserted into the flexible coupling tube are configured to be inserted into the flexible coupling tube in a predetermined direction; and an outer surface of said portion of the connection member configured to be inserted into the flexible coupling tube is configured to engage an inner circumference of said coupling tube in a direction opposite to said predetermined direction.

11. The connecting structure according to claim 10, wherein said flexible sheath is one of a tube or a wound coil pipe.

12. The connecting structure according to claim 9, wherein said flexible sheath is one of a tube or a wound coil pipe.

13. The connecting structure according to claim 2, wherein:

said thickened portion and said portion of the connection member configured to be inserted into the flexible coupling tube are configure to be inserted into the flexible coupling tube in a predetermined direction;

an outer surface of said portion of the connection member configured to be inserted into the flexible coupling tube is configured to engage an inner circumference of said coupling tube in a direction opposite to said predetermined direction.

14. The connecting structure according to claim 13, wherein said flexible sheath is one of a tube or a wound coil pipe.

15. The connecting structure according to claim 2, wherein said flexible sheath is one of a tube or a wound coil pipe.

* * * * *